United States Patent [19]

James et al.

[11] Patent Number: 4,865,851

[45] Date of Patent: Sep. 12, 1989

[54] PHARMACEUTICAL COMPOSITION COMPRISING CEFUROXIME AXETIL

[75] Inventors: Michael B. James, Bishop's Stortford; Leonard G. Elliott, Low Midtown, both of England

[73] Assignee: Glaxo Group Limited, London, England

[21] Appl. No.: 193,784

[22] Filed: May 13, 1988

[30] Foreign Application Priority Data

May 14, 1987 [GB] United Kingdom ............... 8711432
Feb. 9, 1988 [GB] United Kingdom ............... 8802926

[51] Int. Cl.$^4$ .............................................. A61K 9/16
[52] U.S. Cl. ................................... 424/498; 424/493; 424/494; 424/495; 424/497
[58] Field of Search ............... 424/498, 493, 495, 497

[56] References Cited

U.S. PATENT DOCUMENTS

| | | | |
|---|---|---|---|
| 2,921,883 | 1/1960 | Reese et al. | 424/498 X |
| 3,926,817 | 12/1975 | Nakajima et al. | 424/498 X |
| 3,960,757 | 6/1976 | Morishita et al. | 424/498 X |
| 4,302,440 | 11/1981 | John et al. | 424/480 X |
| 4,533,542 | 8/1985 | Buddenbaum et al. | 424/498 X |
| 4,609,542 | 9/1986 | Panoz et al. | 424/498 |
| 4,713,245 | 12/1987 | Ando et al. | 424/498 X |
| 4,764,375 | 8/1988 | Paradissis | 424/498 X |

FOREIGN PATENT DOCUMENTS 2181052A 4/1987 United Kingdom .

Primary Examiner—Thurman K. Page
Attorney, Agent, or Firm—Bacon & Thomas

[57] ABSTRACT

Cefuroxime axetil in particulate form is coated with an integral coating of a lipid or mixture of lipids which serves to mask the bitter taste of cefuroxime axetil but disperses or dissolves on contact with gastrointestinal fluid. The resulting particles may be incorporated into pharmaceutical compositions for oral administration, for instance aqueous suspensions.

33 Claims, No Drawings

PHARMACEUTICAL COMPOSITION COMPRISING CEFUROXIME AXETIL

This invention is concerned with pharmaceutical compositions containing the 1-acetoxyethyl ester of cefuroxime, which has the approved name 'cefuroxime axetil'.

cefuroxime, as disclosed in British Patent Specification No. 1453049, is a valuable broad spectrum antibiotic characterised by high activity against a wide range of gram-positive and gram-negative microorganisms, this property being enhanced by the very high stability of the compound to $\beta$-lactamases produced by a range of gram negative microorganisms. Cefuroxime and its salts are principally of value as injectable antibiotics since they are poorly absorbed from the gastro-intestinal tract.

We have found that esterification of the carboxyl group of cefuroxime as a 1-acetoxyethyl ester to give cefuroxime axetil improves the effectiveness on oral administration as disclosed in British Patent Specification No. 1571683. The presence of the 1-acetoxyethyl esterifying group results in significant absorption of the compound from the gastro-intestinal tract, whereupon the esterifying group is hydrolysed by enzymes present in, for example, serum and body tissues to yield the antibiotically active acid. It is particularly advantageous to employ cefuroxime axetil in an amorphous form as disclosed in British Patent Specification No. 2127401.

Cefuroxime axetil has therefore extended the valuable therapeutic potential of cefuroxime by making available a form of the antibiotic which may be administered orally rather than by injection only.

A convenient means of presenting antibiotics for oral administration is in the form of granules which may be administered as a solution or suspension or taken with a draught of water. Solutions or suspensions of granules as, for example, a syrup are particularly convenient for oral administration of antibiotics to children. However, cefuroxime axetil has an extremely bitter taste which is long lasting and which cannot be adequately masked by the addition of sweeteners and flavours to conventional granule presentations.

Another problem arises from the tendency of cefuroxime axetil, both in crystalline form and the amorphous form mentioned above, to form a gelatinous mass when contacted with aqueous media. This gelling effect is temperature dependent but does occur at temperatures of about 37° C., i.e. at the physiological temperatures at which the disintegration of an orally administered granule would take place. Where there is a relatively slow dispersion of cefuroxime axetil into the surrounding aqueous medium following ingestion, there is the risk that cefuroxime axetil present in the composition may gel. Such gel formation would lead to poor dissolution of the cefuroxime axetil and hence poor absorption from the gastrointestinal tract, i.e. low bioavailability. In the case of granule formulations the use of particles of small diameter and high surface area is desirable to avoid such gelling.

In the formulation of cefuroxime axetil into granules it is important to avoid release of the drug into any liquid suspension which is used or, indeed, into the mouth. Such problems may be minimised by formulating the cefuroxime axetil as lipid coated particles the coat of which has limited permeability to water. Any holes in the coating would mean that the bitter taste was not effectively masked and it is important therefore that the coating is integral.

We have thus found that the extremely bitter taste of cefuroxime axetil may be overcome by the application to cefuroxime axetil particles of integral lipid coatings which are substantially insoluble in water but which are readily dispersed or dissolved in gastro-intestinal fluid. The formulated coated particles, while not releasing the bitter cefuroxime axetil in the wet environment of the mouth, break down upon contact with gastro-intestinal fluid, thus allowing rapid dispersion and dissolution in the gastro-intestinal tract.

British Patent Specification No. 2081092 discusses the use of wax (i.e. lipid) coatings for the purpose of masking the bitterness of medicinal substances. It is however explained at page 1, line 4, to page 2, line 5, that the use of wax coatings results in poor dissolution of the medicinal substances in the alimentary canal as exemplified by compositions described in British Patent Specification No. 1323161 which contain penamecillin coated with lipids containing hydrogenated castor oil; it is proposed in British Patent Specification No. 2081092 to overcome this problem by mixing the waxes used with water-swellable materials. This would clearly not be appropriate for cefuroxime axetil granules which when made up into aqueous suspensions must retain their taste masking properties on storage for up to 14 days. If a coating containing water-swellable materials were to be used, then inevitably the taste masking effect of the coating would be lost on storage in aqueous media for this period of time.

Lipid coatings have hitherto also been used to give free flowing powders (see for instance U.S. Pat. No. 3,247,065) and in the preparation of sustained release medicaments which may be formulated as tablets or capsules (see for instance U.S. Pat No. 3,146,167). These products have however in general been of much larger particle size than would be acceptable for incorporation into an aqueous suspension for oral administration. Moreover in view of: (i) the past use of lipid coatings to provide sustained release medicaments, (ii) the problem of low bioavailability of the medicinal substance where wax coatings are used as described in British Patent Specification No. 2081092 and (iii) the known tendency for cefuroxime axetil to gel with consequent poor absorption from the gastro-intestinal tract, it is particularly surprising that cefuroxime axetil particles provided with integral lipid coatings do allow rapid dispersion and dissolution in the gastro-intestinal tract and thus do enable acceptable levels of bioavailability to be achieved.

According to one aspect of the invention therefore we provide a composition comprising cefuroxime axetil in particulate form, the particles being provided with integral coatings of a lipid or a mixture of lipids which are insoluble in water and which serve to mask the bitter taste of cefuroxime axetil upon oral administration but which disperse or dissolve on contact with gastro-intestinal fluid.

In order to provide taste-masked particles of cefuroxime axetil suitable for oral administration the melting point of the lipid used should be sufficiently high to prevent melting of the coated particles in the mouth, thereby leading to release of the bitter tasting active ingredient, but not so high that the cefuroxime axetil active ingredient itself melts and/or becomes chemically degraded during the coating process. Thus the lipid or mixture of lipids for use in the present invention will conveniently have a melting point of from 30° to 80° C. and preferably from 40° to 70° C. Where the composition according to the invention contains amorphous cefuroxime axetil, the melting point of the lipid or mixture of lipids is still more preferably from 45° to 60° C.

Suitable lipids include fatty acids or monohydric alcohols thereof, fixed oils, fats, waxes, sterols, phospholipids and glycolipids. The lipid may, for example, be a high molecular weight ($C_{10-30}$) straight chain saturated or unsaturated aliphatic acid, such as stearic acid or palmitic acid; a triglyceride for example a glyceryl ester of a high molecular weight ($C_{10-30}$) aliphatic acid, such as glyceryl trilaurate or glyceryl trimyristate; a partially hydrogenated vegetable oil such as cottonseed oil or soyabean oil; a wax for example beeswax or carnauba wax; a high molecular weight ($C_{10-30}$) straight chain aliphatic alcohol such as stearyl alcohol or cetyl alcohol; or a mixture thereof. Mixtures of high molecular weight fatty acids such as mixtures of stearic and palmitic acids, mixtures of high molecular weight straight chain aliphatic alcohols, such as cetostearyl alcohol, mixtures of partially hydrogenated cottonseed and soyabean oils and mixtures of high molecular weight aliphatic acids and glyceryl esters such as a mixture of stearic acid and glyceryl trilaurate may, for example, be used. A particularly preferred lipid providing good bioavailability and having physical properties particularly compatible with cefuroxime axetil is stearic acid in admixture with palmitic acid in a ratio in the range 3:7 to 7:3 by weight, more preferably about 1:1 by weight.

The composition of the invention may contain cefuroxime axetil in crystalline form or more preferably in amorphous form, for example as described in British Patent Specification No. 2127401.

If desired, the cefuroxime axetil may be first undercoated with a substance with coating properties. This undercoating may serve to protect the cefuroxime axetil where it may be chemically sensitive to the lipid with which it is coated.

The substance with coating properties used for the undercoating is preferably water-soluble and is preferably a film-forming agent. Film-forming agents which are useful include polysaccharides such as maltodextrin, alkylcelluloses such as methyl or ethyl cellulose, hydroxyalkylcelluloses (e.g. hydroxypropylcellulose or hydroxypropylmethylcelluloses), polyvinylpyrrolidone and polymers based on methacrylic acid. These may be applied from aqueous or non-aqueous systems as appropriate. Maltodextrin is particularly preferred. Undercoated particles in which the cefuroxime axetil is present at a concentration of 10 to 30% by weight, for example about 20% by weight may conveniently be used for coating by the lipid.

The lipid coated particles according to the invention will preferably contain from 5 to 90%, more preferably from 5 to 50% and still more preferably from 5 or 10 to 30% by weight of cefuroxime axetil. Where the cefuroxime axetil is first undercoated the lipid coated particles most preferably contain from 5 to 15% by weight of cefuroxime axetil; where no undercoating is employed the lipid coated particles most preferably contain from 10 to 30% by weight of cefuroxime axetil.

In general, particles provided with an integral lipid coating to mask the bitter taste of the cefuroxime axetil can have a diameter of less than 250 microns. Coated particles with diameters in the range of from 1 to 250 microns are thus preferred. The size of the coated particles is an important factor with respect to the bioavailability of the cefuroxime axetil and the acceptability of such products for oral administration, average particle sizes in excess of about 250 microns mean diameter by volume giving an undesirable gritty taste. Pharmaceutical products according to the invention will thus generally take the form of coated particles having a mean diameter by volume of less than 100 microns, e.g. in the range of 20 to 100 microns or more especially 30 to 60 microns. It is convenient to apply the integral lipid coatings to particles which prior to coating have a mean diameter by volume of less than 80 microns, e.g. in the range of 5 to 50 microns. For example, amorphous cefuroxime axetil can be prepared in the form of hollow microspheres having a mean diameter by volume in the range of 5 to 50 microns by a spray-drying method as described in British Patent Specification No. 2127401.

The coated particles of the invention may conveniently be prepared by atomising a dispersion of particulate cefuroxime axetil in a molten lipid and cooling the coated particles thereby obtained and such a process constitutes a further feature of the invention. The dispersion may be prepared by adding particulate cefuroxime axetil to the molten lipid or mixture of lipids or alternatively mixing the ingredients of the dispersion together in the solid state and then melting the lipid or mixture of lipids.

The particulate cefuroxime axetil can be dispersed in the molten lipid using conventional techniques, for example, using a high shear mixer. Generally, the temperature of the molten lipid will be 10° to 20° C. above its melting point.

A particularly preferred dispersion for preparing lipid coated particles of cefuroxime axetil is a dispersion of cefuroxime axetil in a mixture of stearic acid and palmitic acid in a ratio in the range 3:7 to 7:3 by weight, preferably in the ratio of about 1:1 by weight. The amount of cefuroxime axetil in the dispersions for preparing lipid-coated particles according to the invention is calculated to provide the desired amount of cefuroxime axetil in the coated particle as discussed above. The molten dispersion is atomised to give particles of lipid-coated cefuroxime axetil on cooling. Techniques which may be used include the use of conventional atomisers such as rotary atomisers, pressure nozzles, pneumatic nozzles and sonic nozzles.

The use of a pneumatic nozzle and in particular a two-fluid internal or external mixing pneumatic nozzle atomiser fitted in a standard spray drying/chilling apparatus is particularly convenient. A suitable internal mixing two fluid nozzle is as for example described in British Patent Specification No. 1412133.

In the atomisation process using an internal mixing two-fluid nozzle atomiser, which atomisation process constitutes a preferred feature of the invention, the molten lipid dispersion of defuroxime axetil will generally be supplied to the atomiser head at a temperature in the range of 60° to 80° C., preferably 65° to 75° C., the precise temperature depending on the particular lipid material to be used. The atomising gas supplied to the nozzle may be air or an inert gas such as dry nitrogen. The temperature of the gas will generally be within the range 60° to 90° C., preferably 70° to 85° C. with the precise temperature dependent upon the particular lipid material being used. We have found that in the coating process, the temperature at which the molten dispersion is maintained is preferably in the range of 10° to 20° C.

above the melting point of the lipid or mixture of lipids used in order to provide a dispersion having the desired viscosity for atomisation. The atomising pressure is desirably controlled in order to produce coated particles of preferred size as referred to above.

The coated particles may be solidified and collected by conventional techniques. The coated particles may conveniently be solidified by applying a stream of cool air or preferably dry nitrogen to the spray chamber at a temperature of for example 0° to 30° C., preferably 5°–20° C. such that cooling and solidification of the particles is complete. The product may for example be collected using a cyclone separator, a dust filter, or under gravity.

Where cefuroxime axetil for dispersion in the lipid material is undercoated, the undercoating substance may be applied to the cefuroxime axetil using conventional coating techniques, for example, spray coating using a fluidised bed granulator, a centrifugal fluidised bed coater or a spray drier or coating with a rotary granulator. In the preparation of lipid coated particles by the process described above, the concentration of undercoated cefuroxime axetil in the molten dispersion is conveniently in the range of 20 to 80% by weight, more conveniently 35 to 65% by weight. The lipid coating thus preferably provides 20 to 80%, most preferably 35 to 65%, by weight of coated particles according to the invention which are prepared from undercoated cefuroxime axetil.

The particulate products according to the invention may be used in pharmaceutical compositions for oral administration and may be presented as a suspension for administration, as a dry product for constitution with water or other suitable vehicle before use for administration as a suspension, or for direct administration and then washed down with water or other suitable liquid. Such preparations may be prepared by conventional means with pharmaceutically acceptable additives such as suspending and/or binding agents e.g. alkylcelluloses such as methyl cellulose, hydroxyalkylcelluloses such as hydroxypropylcellulose and hydroxypropylmethylcellulose, sodium carboxymethylcellulose or mixtures thereof, pregelatinised maize starch or polyvinylpyrrolidone; fillers, e.g. sucrose, starch, lactose and microcrystalline cellulose; adsorbents and flow aids such as talc, aluminium oxide and silicon dioxide; emulsifying or thickening agents e.g. lecithin or aluminium stearates; surface active agents, e.g. sodium lauryl sulphate or non-ionic polyoxyethylenepolyoxypropylene copolymers; preservatives e.g. methyl or propyl hydroxybenzoates or sorbic acid; colouring agents, e.g. titanium dioxide pigments, lake colours and iron oxide pigments; flavouring agents e.g. 'mint' flavours such as peppermint flavouring agents; and bulk sweeteners e.g. sorbitol and sucrose or artificial sweeteners e.g. saccharin sodium and sodium cyclamate.

Where the additives are in solid form, the particles of the invention may be blended with the additives in the form of a dry mix or the additives may themselves be formulated into an excipient granule for blending with the active particles of the invention, or more preferably the particles of the invention may be granulated together with the additives using conventional techniques.

Such granulation techniques include the use of conventional granulators e.g. spray granulators, rotary granulators, centrifugal fluidised bed granulators, high speed mixer granulators and extrusion and comminution techniques. Drying may be carried out by conventional techniques, for example in the granulator or in a drying oven or hot air drier. It is, of course, desirable that the granules should be prepared by a method which is convenient to provide granules of the desired size; this may generally be achieved by conventional adjustment of the conditions of granulation and, if necessary, by screening of the granules thus produced.

Where the pharmaceutical composition for oral administration is presented as a suspension, this may be in an aqueous or non-aqueous vehicle provided this is compatible with the lipid coating material. Suitable non-aqueous vehicles for suspension include, for example, almond oil, fractionated coconut oil or oily esters.

In a further aspect, therefore, the invention provides a pharmaceutical composition for oral administration comprising a composition according to the invention together with one or more pharmaceutical carriers or excipients.

In particular there is provided a granule for oral administration comprising the coated particles of cefuroxime axetil of the invention together with one or more pharmaceutically acceptable excipients. The excipient material preferably comprises a sweetener, for example sucrose. Other pharmaceutically acceptable excipients which may be present include those described above. The granules may be prepared using conventional methods as described above. Granulation may be achieved, for example, by blending of the ingredients, and granulation with water. The resulting granules may be passed through a screen to remove particles of too large a size. Granules of a diameter below 1000 microns, and particularly below 800 microns are preferred.

Where the particles of the invention are formulated in an aqueous medium, this advantageously contains an orally acceptable solute at relatively high concentration since this assists in maintaining the taste-masking properties of the lipid coating. Thus, for example, the aqueous medium may contain a sugar, e.g. sucrose, advantageously in the concentration range 50 to 85 weight percent, preferably 60 to 80 weight percent. Such a solute can conveniently be incorporated into the granules containing the particulate product according to the invention. In the case of sucrose this also serves as a sweetener and preservative.

The pharmaceutical products of the invention, formulated for oral administration as a suspension, may be constituted with a suitable quantity of water, for use in oral administration of cefuroxime axetil. The particles will typically be presented so as to give a multidose suspension containing the equivalent of 500 mg to 10 g cefuroxime or a single dose suspension containing the equivalent of 100–1000 mg cefuroxime.

Doses employed for human treatment will typically be in the range 100–3000 mg cefuroxime per day, e.g. 250 to 2000 mg cefuroxime per day for adults and 125 to 1000 mg cefuroxime per day for children, although the precise dose will depend on inter alia the frequency of administration.

The following Examples illustrate the invention.

The cefuroxime axetil used in the Examples was highly pure spray dried amorphous material prepared as described in British Patent Specification No. 2127401 with a mean particle diameter by volume in the range 5–50 microns ($\mu$m).

Revel A is a commercial food grade of stearic acid, Hyfac is a commercial grade of stearic acid, Dynasan 112 is glyceryl trilaurate and Dynasan 114 is glyceryl trimyristate. Revel A, Hyfac, Dynasan 112 and Dynasan 114 are all tradenames.

Stearic acid BPC is specified as a mixture of fatty acids, chiefly stearic and palmitic acids in the British Pharmaceutical Codex (1973). In the United States 'National Formulary XV, 1980', stearic acid USNF is specified as containing not less than 40% stearic acid, not less than 40% palmitic acid and not less than 90% of stearic and palmitic acids.

Particle size measurements for Examples 1 to 3 were made by optical microscopy, Coulter Counter and laser light scattering using the following methods:

1. Optical Microscopy

A small sample of lipid coated material was suspended on a microscope slide in silicone fluid and the particles were viewed and counted at ×100 magnification using an Imanco FMS microscope.

For each batch two slides were prepared and nine fields counted per slide. The particles were sized relative to a British Standard graticule (BS 3406, 1961) and assigned to size bands ranging from >60 μm to <7.5 μm. The number count in each size band was recorded and used to calculate a volume mean diameter (VMD) using the following formula:

$$\frac{\sum_{i=1}^{m} N(\chi_i) \chi_i^4}{\sum_{i=1}^{m} N(\chi_i) \chi_i^3}$$

$N(\chi_i)$ = number in given size band
$\chi_i$ = mid point of size band

2. Coulter Counter

A small sample of lipid coated material was suspended in Coulter dispersant on a microscope slide. A quantity of this dispersed sample was added to the measuring beaker of the Coulter Counter, containing a 1% solution of sodium chloride in distilled water filtered through a 0.45 μm Millipore filter, until the concentration index on the Coulter Counter (model TAII) registered between 5 and 10%. The beaker contents were then sonicated for 30 seconds, replaced in the Coulter Counter and stirred for one minute before a reading was taken. A number count was taken of particles in a number of size bands in the range 8.0 μm to 128.0 μm. The count was repeated after a total of four minutes stirring.

A mean of the one and four minute counts was taken for each size band and used to calculate a VMD (formula as described in Method 1).

The measurement was repeated from the start of sample preparation for a minimum of five separate samples per batch. The five VMD values were averaged to give a single composite mean.

Except where otherwise stated all the references herein to mean diameters by volume were measured by the Coulter Counter method.

3. Laser Light Scattering

A 5 mg sample of lipid coated material was added to 5 ml of 0.25% Tween 80 in distilled water and sonicated for 60 seconds. The sample vial was inverted twice, to mix the contents, and the sample was then added dropwise to the measuring cell of a Malvern 3600 E-type Particle Sizer until a beam obscuration of 0.2 was obtained. Readings were taken after one and four minutes stirring in the sample cell.

The VMD value for each sample was calculated. Measurements on a minimum of five samples were carried out on each batch and a composite mean produced.

Example 1

A dispersion of amorphous cefuroxime axetil (150 g) in Stearic Acid powder BPC (850 g) was prepared by melting the lipid, raising the temperature of the molten lipid to a temperature of about 15° C. above its melting point and adding the cefuroxime axetil with mixing.

The molten lipid/cefuroxime axetil dispersion was fed into a spray drier/chiller apparatus using a peristaltic pump and atomised using an external mixing two fluid nozzle [nozzle outlet dimensions 2.54 mm (liquid orifice) and 3.81 to 4.57 mm (annular atomising fluid orifice)] with air at a temperature of 65°–70° C. and an atomising pressure of about 345 kPa (50 psi). The product was chilled using a stream of air fed into the spray chamber at ambient temperature and the solidified product was collected in a cyclone separator.

Examples 2

A dispersion of amorphous cefuroxime axetil (150 g) in Stearic Acid powder BPC (850 g) was prepared from a dry mix of the ingredients by melting the lipid, and holding the temperature at about 15° C. above the melting point of the lipid.

The molten lipid/cefuroxime axetil dispersion was pumped into a spray drier/chiller apparatus at a rate of 300–500ml/minute and atomised using an internal mixing two fluid nozzle (supplied by Delavan Limited, Widnes, Cheshire catalogue number 32163-1 and as described in British Patent Specification No. 1412133) with air at a temperature of 65°–70° C. and an atomising pressure in the range of 276–345 kPa (40–50 psi). The product was chilled using a stream of air fed into the spray chamber at ambient temperature and the solidified product was collected by gravity.

Example 3

A dispersion of amorphous cefuroxime axetil in Stearic Acid powder BPC was prepared as in Example 2.

The molten lipid/cefuroxime axetil dispersion was pumped using a gear pump into a spray drier/chiller apparatus and atomised using an external mixing two fluid nozzle (2.0 mm bore) with air at a temperature of 75° C. and an atomising pressure of 310 kPa (45 psi). The product was chilled using a stream of air fed into the spray chamber at ambient temperature and the solidified product was collected in a cyclone separator.

The following particle sizes were recorded for batches of material prepared according to the processes described in Examples 1–3:

| EXAMPLE NO | MALVERN 3600 E-TYPE PARTICLE SIZER | COULTER COUNTER TAII | OPTICAL MICROSCOPY IMANCO FMS |
|---|---|---|---|
| 1 | 44.91 μm<br>n = 10 | 48.73 μm<br>n = 5 | 42.07 μm<br>n = 2 |
| 2 BATCH A | 43.93 μm<br>n = 20 | 38.80 μm<br>n = 5 | 40.10 μm<br>n = 2 |
| 2 BATCH B | 55.56 μm<br>n = 10 | 44.43 μm<br>n = 5 | 43.86 μm<br>n = 2 |
| 3 | 29.46 μm<br>n = 10 | 37.21 μm<br>n = 10 | 35.18 μm<br>n = 2 |

All particle sizes are expressed as VMD.

n=number of samples measured.

Example 4

A dry mix of cefuroxime axetil (124 g) and Stearic Acid powder BPC (676 g) was heated to 68° C. with stirring to melt the lipid and form a suspension. The molten lipid/cefuroxime axetil dispersion was transferred to a spray cooling chamber at a rate of about 400 ml/minute by applying pressure to the melt vessel. This was then atomised using an internal mixing two fluid nozzle (as described in Example 2), with air at a temperature of 78° C. and a pressure of 380 kPa (55 psi). The product was cooled in a stream of air fed into the spray chamber and the solidified material collected by gravity. Median particle diameter by volume (Coulter counter) 51 μm Cefuroxime axetil content 15.4%.

Example 5

A dispersion for lipid-coating was prepared by melting the lipid, raising the temperature of the molten lipid to a temperature of 15° C. above its melting point and adding the appropriate amount of cefuroxime axetil with mixing using a high shear mixer.

The molten lipid/cefuroxime axetil dispersion was pumped into a conventional spray drier/chiller apparatus with a spray chamber height of 1.82 m at a rate of approximately 300 ml/minute and atomised using an external mixing two fluid nozzle (as described in Example 1) at an atomising pressure in the range of 275 to 414 kPa (40 to 60 psi). The product was chilled using a stream of air fed into the spray chamber at 7°–11° C. The solid product was collected in a cyclone separator.

The following mixtures of cefuroxime axetil and various lipids were spray chilled to give taste-masked lipid-coated particles of cefuroxime axetil. The diameters of the particles obtained were determined by optical microscopy using a "Quantimet 970" Image Analyser.

| | % w/w | Weight (g) |
|---|---|---|
| (a) Stearic acid powder BPC | 85 | 850 |
| Cefuroxime axetil | 15 | 150 |
| Mean particle diameter by number 7.18 μm (95% of the total particles obtained had a diameter of less than 22 μm.) Mean particle diameter by volume 41.9 μm. | | |
| (b) Hyfac | 85 | 850 |
| Cefuroxime axetil | 15 | 150 |
| Mean particle diameter by number 7.93 μm (95% of the total particles obtained had a diameter of less than 25 μm.) Mean particle diameter by volume 47.5 μm. | | |
| (c) Stearic acid powder BPC | 42.5 | 212.5 |
| Dynasan 112 | 42.5 | 212.5 |
| Cefuroxime Axetil | 15 | 75.0 |
| Mean particle diameter by number 8.38 μm (95% of the total particles obtained had a diameter of less than 32 μm.) Mean particle diameter by volume 51.0 μm. | | |
| (d) Dynasan 114 | 85 | 425 |
| Cefuroxime axetil | 15 | 75 |
| Mean particle diamter by number 7.32 μm (95% of the total particles obtained had a diameter of less than 21 μm.) Mean particle diameter by volume 47.1 μm. | | |

Example 6

Maltodextrin coated cefuroxime axetil particles were prepared by dispersing maltodextrin (400 g), tutti-frutti flavour (1 g) and starch 1500 (25 g) in distilled water (to 1 L) by high shear mixing. Cefuroxime axetil (100 g) was dispersed in this suspension using high shear mixing and the suspension was then spray dried using conventional spray drying techniques. The product was collected in a cyclone separator.

The maltodextrin coated cefuroxime axetil was then coated with Stearic acid BPC as described in Example 5.

| | % w/w | Weight (g) |
|---|---|---|
| Stearic acid powder BPC | 60 | 600 |
| Maltodextrin coated cefuroxime axetil | 40 | 400 |
| Mean particle diameter by number 7.51 μm (95% of the total particles obtained had a diameter of less than 23 μm). Mean particle diamter by volume 46.0 μm. | | |

Example 7

Using the processes described in Examples 5 and 6 the following mixtures of cefuroxime axetil and various lipids were spray chilled to give taste-masked lipid-coated particles of cefuroxime axetil.

| | % 2/2 | Weight (g) |
|---|---|---|
| (a) Stearic acid powder BPC | 55 | 611 |
| Maltodextrin coated cefuroxime axetil | 45 | 500 |
| (b) Stearic acid powder BPC | 80 | 800 |
| Cefuroxime axetil | 20 | 200 |
| (c) Revel A | 80 | 800 |
| Cefuroxime axetil | 20 | 200 |
| (d) Cetostearyl alcohol | 85 | 850 |
| Cefuroxime axetil | 15 | 150 |
| (e) Cetostearyl alcohol | 60 | 600 |
| Maltodextrin coated cefuroxime axetil | 40 | 400 |
| (f) Hyfac | 60 | 600 |
| Maltodextrin coated cefuroxime axetil | 40 | 400 |
| (g) Stearic acid powder USNF | 90 | 900 |
| Cefuroxime axetil | 10 | 100 |
| (h) Stearic acid powder USNF | 40 | 200 |
| Dynasan 112 | 40 | 200 |
| Cefuroxime axetil | 20 | 100 |
| (i) Stearic acid powder BPC | 42.5 | 212.5 |
| Dynasan 114 | 42.5 | 212.5 |
| Cefuroxime axetil | 14 | 75 |
| (j) Stearic acid | 42.5 | 212.5 |
| Palmitic acid | 42.5 | 212.5 |
| Cefuroxime axetil | 15 | 75 |
| (k) Stearic acid | 40 | 200 |
| Palmitic acid | 40 | 200 |
| Cefuroxime axetil | 20 | 100 |

Pharmaceutical Example

Stearic Acid BPC coated cefuroxime axetil is combined with sucrose and a proprietary flavouring in the proportions shown below. These materials are blended, then granulated by conventional means using water as the granulation fluid. After drying, the granules may be screened to remove any agglomerates, and they are then filled into bottles. A suspension for oral administration is produced by constitution with water to provide 125 mg of cefuroxime per 5 ml of suspension.

| Ingredient | % w/w |
|---|---|
| Stearic Acid BPC coated cefuroxime axetil | 24.92 |
| Sucrose | 74.75 |
| Flavour (fruits of the forest) | 0.33 |

We claim:

1. A composition comprising cefuroxime axetil in particulate form, the particles being provided with integral coatings of a lipid or a mixture of lipids which are insoluble in water and which serve to mask the bitter taste of cefuroxime axetil upon oral administration but which disperse or dissolve on contact with gastro-intestinal fluid.

2. A composition as claimed in claim 1 wherein the lipid or mixture of lipids has a melting point in the range of from 30° to 80° C.

3. A composition as claimed in claim 2 wherein the lipid or mixture of lipids has a melting point in the range of from 40° to 70° C.

4. A composition as claimed in claim 1 wherein the lipid or mixture of lipids comprises one or more straight chain aliphatic carboxylic acids having from 10 to 30 carbon atoms.

5. A composition as claimed in claim 4 wherein the mixture of lipids comprises a mixture of stearic and palmitic acids in a ratio of from 3:7 to 7:3 by weight.

6. A composition as claimed in claim 5 wherein the mixture of stearic and palmitic acids is in a ratio of about 1:1 by weight.

7. A composition as claimed in claim 1 containing from 5 to 90% by weight of cefuroxime axetil.

8. A composition as claimed in claim 7 containing from 10 to 30% by weight of cefuroxime axetil.

9. A composition as claimed in claim 1 containing amorphous cefuroxime axetil.

10. A composition as claimed in claim 9 wherein the cefuroxime axetil is spray-dried cefuroxime axetil in the form of hollow microspheres.

11. A composition as claimed in claim 1 wherein the coated particles have diameters in the range from 1 to 250 microns.

12. A composition as claimed in claim 1 wherein the coated particles have a mean diameter by volume of less than 100 microns.

13. A process for the preparation of a composition as claimed in claim 1 which comprises dispersing particulate cefuroxime axetil in a molten lipid or mixture of lipids, atomising the dispersion to provide particles having integral coatings of the lipid or mixture of lipids and cooling and collecting the coated particles thereby obtained.

14. A process as claimed in claim 13 wherein the lipid or mixture of lipids has a melting point in the range of from 30° to 80° C.

15. A process as claimed in claim 14 wherein the lipid or mixture of lipids has a melting point in the range of from 40° to 70° C.

16. A process as claimed in claim 13 wherein the lipid or mixture of lipids comprises one or more straight chain aliphatic carboxylic acids having from 10 to 30 carbon atoms.

17. A process as claimed in claim 16 wherein the mixture of lipids comprises a mixture of stearic and palmitic acids in a ratio of from 3:7 to 7:3 by weight.

18. A process as claimed in claim 17 wherein the mixture of stearic and palmitic acids is in a ratio of about 1:1 by weight.

19. A process as claimed in claim 13 wherein the dispersion is atomised by a pneumatic nozzle atomiser.

20. A process as claimed in claim 19 wherein the atomiser is an internal mixing two-fluid nozzle atomiser.

21. A process as claimed in claim 19 wherein the molten dispersion is atomised at a temperature which is in the range of 10° to 20° C. above the melting point of the lipid or mixture of lipids used.

22. A process as claimed in claim 19 wherein the particulate cefuroxime axetil prior to coating has a mean particle diameter by volume in the range of from 5 to 20 microns.

23. A process as claimed in claim 19 wherein the amounts of particulate cefuroxime axetil and lipid or lipid mixture used are such as to provide coated particles containing from 5 to 50% by weight of cefuroxime axetil.

24. A process as claimed in claim 23 wherein the amounts of particulate cefuroxime axetil and lipid or lipid mixture used are such as to provide coated particles containing from 5 to 30% by weight of cefuroxime axetil.

25. A process as claimed in claim 19 wherein the dispersion is atomised to provide coated particles having diameters in the range from 1 to 250 microns.

26. A process as claimed in claim 19 wherein the dispersion is atomised to provide coated particles having a mean diameter by volume of less than 100 microns.

27. A process as claimed in claim 26 wherein the dispersion is atomised to provide coated particles having a mean diameter by volume of from 20 to 100 microns.

28. A process as claimed in claim 27 wherein the dispersion is atomised to provide coated particles having a mean diameter by volume of from 30 to 60 microns.

29. A pharmaceutical composition for oral administration comprising a composition as claimed in claim 1 together with one or more pharmaceutical carriers or excipients.

30. A pharmaceutical composition as claimed in claim 29 in the form of granules.

31. A pharmaceutical composition as claimed in claim 29 in the form of an aqueous suspension.

32. A pharmaceutical composition as claimed in claim 31 containing an orally acceptable solute serving to assist in maintaining the taste-masking properties of the lipid coating.

33. A pharmaceutical composition as claimed in claim 32 wherein the solute is sugar in the concentration range 50 to 85 weight percent.

* * * * *